US005356783A

United States Patent [19]

Buonassisi et al.

[11] Patent Number: 5,356,783

[45] Date of Patent: Oct. 18, 1994

[54] INHIBITOR OF TISSUE FACTOR ACTIVITY

[75] Inventors: Vincenzo Buonassisi; Patricia C. Colburn, both of Lake Placid, N.Y.

[73] Assignee: W. Alton Jones Cell Science Center, Inc., Lake Placid, N.Y.

[21] Appl. No.: 8,586

[22] Filed: Jan. 25, 1993

Related U.S. Application Data

[60] Division of Ser. No. 830,462, Feb. 5, 1992, Pat. No. 5,219,994, which is a continuation of Ser. No. 707,314, May 29, 1991, abandoned, which is a continuation of Ser. No. 268,893, Nov. 8, 1988, abandoned.

[51] Int. Cl.[5] .................. C07K 15/28; G01N 33/535; G01N 33/577; A61K 39/395

[52] U.S. Cl. .................................. 435/7.9; 530/389.3; 530/388.25; 435/7.92; 436/548

[58] Field of Search ............ 530/388.25, 389.3, 387.9; 435/7.92, 7.93, 7.95, 13, 70.21, 7.9; 436/518, 536, 542, 548

[56] References Cited

U.S. PATENT DOCUMENTS

| | | | |
|---|---|---|---|
| 4,966,852 | 10/1990 | Wun et al. | 435/69.2 |
| 5,219,994 | 6/1993 | Buonassisi et al. | 530/380 |

OTHER PUBLICATIONS

Warn–Cramer et al, 1987, Partial Purification and Characterization of Extrinsic Pathway Inhibitor (the Factor Xa–Dependent Plasma Inhibitor of Factor VIIa/Tissue Factor). Thrombosis Res 48:11–22.

Warn–Cramer et al, 1992, Purification of Tissue Factor Pathway Inhibitor (TFPI) from Rabbit Plasma and Characterization of its Differences from TFPI Isolated from Human Plasma, Thrombosis Res 67: 367–83.

Wun et al. "Cloning and Characterization of a cDNA Coding for the Lipoprotein–associated Coagulation Inhibitor Shows That it Consists of Three Tandem Kunitz–type Inhibitory Domains" *J. Biol. Chem.* 263(13):6001–6004 (1988).

Colburn et al. "Enhanced Inhibition of Tissue Factor by the Extended Form of an Endothelial Cell Cell Glycoprotein (an Extrinsic Pathway Inhibitor)" *J. Cell. Physiol.* 140:320–326 (1991).

Hjort "Anti Convertin" *Scand. J. Clin Lab. Invest* vol. 9, Suppl 27, pp. 76–97.

Broze et al. Proc Natl Acad Sci USA 84: 1886–1890 (1987).

*Primary Examiner*—Esther M. Kepplinger
*Assistant Examiner*—James L. Grun
*Attorney, Agent, or Firm*—Browdy and Neimark

[57] ABSTRACT

A sulfated glycoprotein with a molecular weight of approximately 45 kda inhibits the activation of tissue factor and thus inhibits the coagulation of blood. This glycoprotein can be used for treatment or prevention of intravascular clotting.

9 Claims, 4 Drawing Sheets

INHIBITOR OF TISSUE FACTOR ACTIVITY

This is a division of application Ser. No. 07/830,462, filed Feb. 5, 1992, now U.S. Pat. No. 5,219,994, which is a continuation of application Ser. No. 07/707,314, filed May 29, 1991, now abandoned, which is a continuation of application Ser. No. 07/268,893, filed Nov. 8, 1988, now abandoned.

FIELD OF THE INVENTION

The present invention is directed to a method and composition for inhibiting the activity of tissue factor.

BACKGROUND OF THE INVENTION

Maintenance of vascular integrity is an important host response to injury- Complex hemostatic mechanisms of coagulation, platelet function, and fibrinolysis exist to minimize adverse consequences of vascular injury and to accelerate vascular repair. Many of these hemostatic mechanisms are initiated and/or regulated by cells of the wall of the blood vessel.

A number of plasma proteins and circulating factors in blood are inactive until the events that stimulate clotting are triggered, at which point the various factors involved in clot formation are activated. Several different types of activation are to be considered in coagulation. One type is the activation of a zymogen of a proteolytic enzyme, the product of which, in turn, activates another zymogen by proteolytic action. Another type does not lead to activation of an enzyme. For example, the proteolytic cleavage of a soluble plasma protein, fibrinogen, results in formation of fibrin, the insoluble protein that forms the clot. Similarly, platelets, the cells that are essential for normal coagulation, must also be activated before they can participate in coagulation.

Classically, the initiation of blood clotting can be conceptually separated into two different, yet similar, molecular mechanisms, called the intrinsic and extrinsic coagulation pathways or cascades. The mechanism of initiation pertaining to this patent application is the extrinsic coagulation pathway. The two pathways converge at a step, the activation of prothrombin to thrombin by factor $X_a$, prior to the actual clot formation. There is also some feedback regulation between the two systems. In the extrinsic pathway, for optimal conditions, each reaction of the coagulation mechanism involves assembly on a cellular surface of a complex that includes a serine protease, a substrate zymogen, and a nonenzymatic cofactor protein, with or without calcium ions. Complex formation on the cell surfaces localizes the hemostatic response, promotes optimal activation of coagulation, and protects proteases from their plasma inhibitors.

The actual set of cascade reactions of the extrinsic pathway are as follows: in the presence of calcium, found in circulation, tissue factor, a membrane-bound procoagulant enzyme, combines with factor VII, a circulating proenzyme, and the complex is activated to TF-$VII_a$ by either $X_a$, which can be found in very low concentrations in the circulating blood, or by high molecular weight kallikrein acting on $XII_a$ of the intrinsic pathway, also found in the circulation. Once the complex has been activated it can active X, a proenzyme in blood, to $X_a$, a serine protease. $X_a$ can now activate, in the presence of factor V, (a cofactor found in circulation), prothrombin to thrombin. Thrombin will then cleave fibrinogen to form fibrin.

Factor V and tissue factor can be synthesized by vascular endothelium, whereas endothelial cells posses binding sites for the plasma proteins, and high molecular weight kininogen, allowing expression of these coagulant activities.

Once thrombin is generated, fibrinogen is cleaved to form fibrin, which is substantially cross-linked by factor $XIII_a$ to form an insoluble fibrin clot. Enmeshed in the clot are platelets that have been recruited to the site of vascular injury after exposure to subendothelial components such as collagen.

When vascular cells are exposed to perturbing stimuli, a number of cellular hemostatic properties are altered, including increased expression of procoagulant activity, decreased expression of anticoagulant activity, and enhanced platelet adhesion and activation.

The coagulation mechanisms can be initiated either by expression of tissue factor activity, (extrinsic pathway), or by activation of factor XII, (intrinsic pathway).

A number of stimuli have been found to induce tissue factor activity. These stimuli include immune modulators such as immune complexes, the monokines interleukin 1 and tumor necrosis factor, other stimuli linked to infection such as endotoxin and microorganisms associated with bacterial endocarditis, a metabolite associated with thrombotic disease (homocysteine), and other stimuli such as mechanical injury and phorbol esters. With the exception of endothelial cell injury induced by mechanical means or by gross infection (such as endocarditis), the induction of these vascular coagulant properties is not normally associated with overt cell injury.

SUMMARY OF THE INVENTION

It is an object of the present invention to inhibit tissue factor activity.

It is another object of the present invention to provide an endothelial cell glycoprotein that inhibits the initiation of the coagulation process promoted by tissue factor.

It is a further object of the present invention to provide a method to maintain blood fluidity.

It is a further object of the present invention to provide compounds for anticoagulant therapy.

It is yet another object of the present invention to provide compounds for prevention and treatment of intravascular clotting.

An endothelial cell glycoprotein that inhibits the initiation of the coagulation process promoted by tissue factor has been identified. This glycoprotein was isolated by heparin-sepharose, hydroxyapatite, and gel filtration chromatography. The N-linked carbohydrate moiety is sulfated.

The endothelial cell product of the present invention is one of the several N-glycan sulfated glycoproteins synthesized by endothelial cells. This molecule has an apparent molecular weight of 45 kDa, having a partial sequence of 22 amino acids, 19 of which were positively identified.

As used herein, the term "salts" includes both salts of carboxyl groups and to acid addition salts of amino groups of the protein molecule. Salts of a carboxyl group may be formed by means known in the art and include inorganic salts, for example, sodium, calcium, ammonium, ferric, or zinc salts, and the like, and salts with organic bases such as those formed, for example, with amines, such as triethanolamine, arginine, or lysine, piperiodine, procaine, and the like. Acid addition salts include, for example, salts with mineral acids such as, for example, hydrochloric acid or sulfuric acid, and salts with organic acids such as, for example, acetic acid or oxalic acid.

Functional derivatives of the glycoproteins according to the present invention include derivatives which may be prepared from the functional groups which occur as side chains on the residues or the N-0 or C-terminal groups, by means known in the art, and are included in the invention as long as they remain pharmaceutically acceptable, i.e., they do not destroy the activity of the protein and do not confer toxic properties on compositions containing it.

These derivatives may include, for example, aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl groups (for example, that of seryl or threonyl residues) formed with acyl moieties.

As "active fractions" of the substantially purified protein, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided that said fraction has the ability to inhibit the activity of tissue factor.

One probable amino acid sequence for the inhibitor of the present invention, wherein the positively identified amino acids are noted in bold type, is as follows, wherein X represents unidentified amino-acids:

$NH_2$-X-X-Glu-Glu-Asp-Glu-Glu-Phe-Thr-X-Ile-Thr-Asp-Ile-Lys-Pro-Pro-Leu-Gln-Lys-Pro-Thr-

BRIEF DESCRIPTION OF THE DRAWINGS

FIG. 1A shows gel filtration chromatography of the hydroxyapatite eluate, and FIG. 1B shows the gel electrophoresis of various materials isolated.

DETAILED DESCRIPTION OF THE INVENTION

Isolation of the Endothelial Cell Inhibitor

Figure 1A:
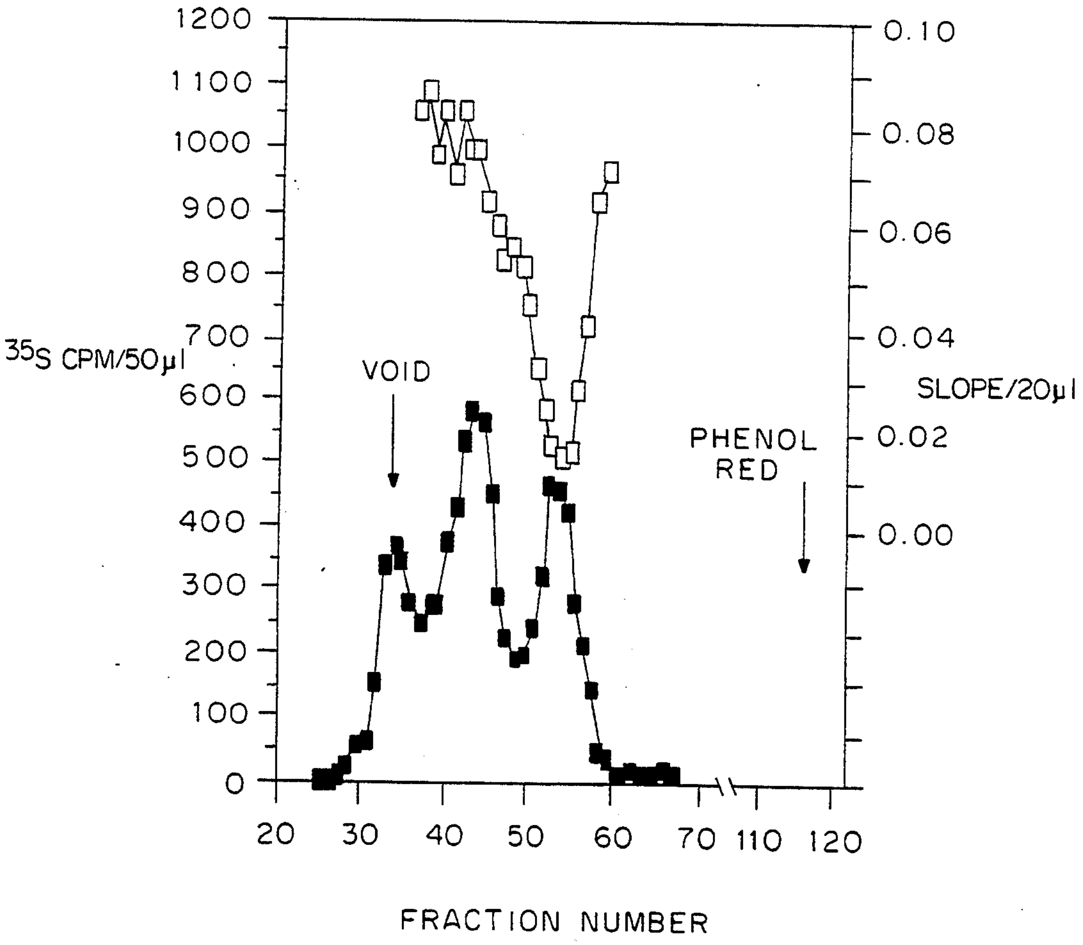
FIGS. 1A and 1B identify the endothelial cell inhibitor of the present invention.

A cell line from the intima of the rabbit aorta was established according to the procedure of Buonassisi et al. as reported in *Proc. Natl. Acad. Sci. USA* 73: (5) 1612-1616, 1976, which article is herein incorporated by reference. This cell line exhibits strict contact inhibition and morphologically resembles intimal endothelial cells. This cell line possesses B-type blood group antigens and fibrinolytic activity. Norepinephrine, acetylcholine, 5-hydroxytryptamine, and phenylephrine increased the levels of both cAMP and cGMP significantly. Propanolol and phentolamine inhibited, respectively, the cAMP and cGMP response to norepinephrine. Angiotensin II and histamine significantly increased cGMP levels but not cAMP levels of the endothelial cells. The cGMP increases with acetylcholine were inhibited by atropine.

conditioned medium, 500 ml, from cell cultures labelled with $H_2{}^{35}SO_4$ was applied to a 1.5×2 cm heparin-Sepharose column. The fractions containing the inhibitory activity, which was eluted with 0.45 M NaCl with a linear NaCl gradient (0.15 M to 1.15 M in 0.02 M sodium phosphate buffer, pH 7.4), were applied to a 1.5 ×1.5 cm hydroxyapatite column. The material present in the bypass was subjected to electrodialysis concentration and fractionated on a 1.5×60 cm Sephacryl S-300 column using as an eluant 0.5 M NaCl in 0.02 M sodium phosphate buffer, pH 7.4. The inhibitor was further purified on a preparative 10% SDS-polyacrylamide gel slab and eluted from the gel by electrodialysis.

The inhibitory activity was estimated with an assay system that included factors VII and X and a chromogenic substrate specific for factor $X_a$: 20 μl of sample was added to 160 μl solution containing 0.05 units factor VII, 0.1 units factor X, and 50 μg bovine serum albumin in 0.02 M sodium phosphate, 0.9% NaCl, pH 7.4. The reaction was initiated by the addition of 40 μl solution containing 22 μl thromboplastin (Sigma, prepared according to instructions from the manufacturer, as a source of tissue factor), 4 μl S-2222 (7 mM), and 14 μl 25 mM $CaCl_2$. The absorbancy at 405 nm was measured over time. The slope of the reaction was determined using the time points where the absorbance increase linearly.

Assay for the Inhibition of Factor X Activation

Five hundred microliters of the incubation mixture contained 0.16 units factor VII, 0.31 units factor X, in buffer (Earle's balanced salt solution), and 60 μl of inhibitor concentrate (hydroxyapatite bypass). The control received 60 μl buffer. Fifty microliters of thromboplastin solution (25 μl thromboplastin in 200 μ25 mM $CaCl_2$) was added to initiate the reaction. The solutions were left at room temperature. At the times indicated, 100 μl was removed from each tube, placed in separate tubes containing 50 μl sample buffer (10% SDS, 20% 2-mercaptoethanol, 30% glycerol) and boiled for five minutes. Fifty microliters were analyzed by analytical SDS-polyacrylamide gel. After electrophoresis, the proteins were transferred to nitrocellulose, and factor X and its fragments were detected using a rabbit anti-human factor X-peroxidase antibody.

Site of Inhibition of the Coagulation Pathway

For the experiments described herein, the methodology was as follows: Ten microliters of inhibitor (hydroxyapatite bypass) was added to tubes containing 150 μl non-conditioned medium supplemented with 10% fetal bovine serum as a source of clotting factors and increasing amounts of factor VII. Control samples contained 10 μl buffer in place of the inhibitor. The reaction was initiated with the addition of 20 μl thromboplastin-substrate solution: 25 μl thromboplastin, 25 μl S-2238 (15 mM, a substrate specific for thrombin), 200 μl 25 mM $CaCl_2$. The amount of thromboplastin present in this reaction mixture was adjusted for the various samples when the experiments requiring increasing amounts of tissue factor were performed.

Similar results are obtained when the assays are performed with purified factors. In the experiments described herein, the reaction rate was strictly dependent on the addition of factor VII and was the same in control samples containing zero units of factor VII as in the samples containing the inhibitor.

Figure 1B:
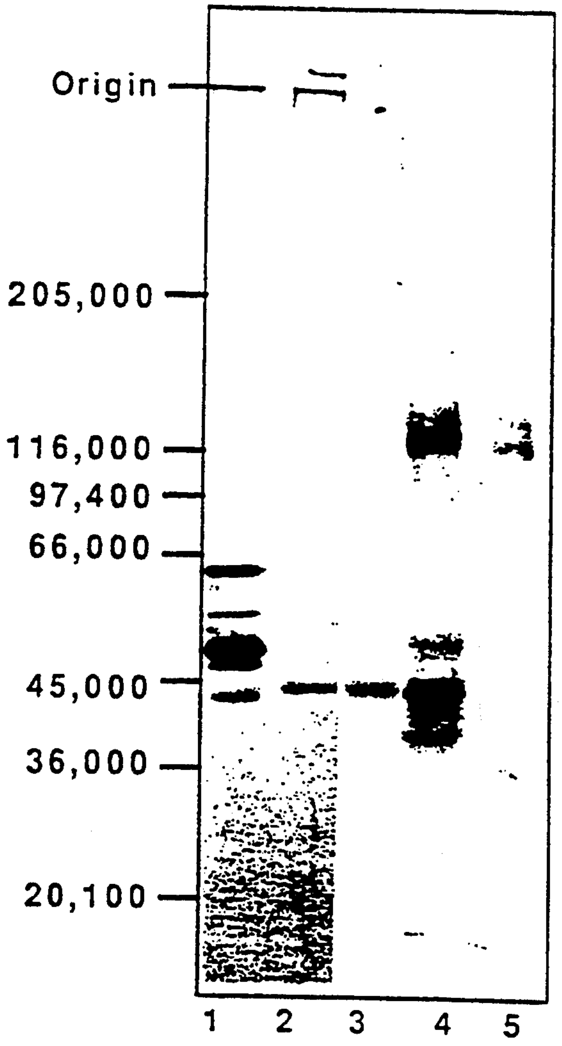

The molecule responsible for the inhibitory activity is a species that can be initially concentrated on a heparin-Sepharose column and which is further purified by hydroxyapatite and gel filtration chromatography. This species can be finally isolated in a highly active state and free of other proteins by polyacrylamide gel electrophoresis, as shown in FIGS. 1A and 1B. This endothelial cell product is one of the several N-glycan sulfated glycoproteins synthesized by this cell type.

To identify the endothelial cell inhibitor of the present invention, as shown in FIGS. 1A and 1B, the molecule was purified from $^{35}$S-labelled conditioned medium by heparin-Sepharose, hydroxyapatite, and gel filtration chromatography- The material present in the peak of activity from the gel filtration column (which contained only one $^{35}$S-labelled species) was subjected to preparative polyacrylamide gel electrophoresis. The active material was eluted from the gel slab, and an aliquot was rerun on an analytical gel. In FIG. 1A, the gel filtration chromatography of the hydroxyapatite eluate is as follows: ■—■, $^{35}$S-radioactivity; □—□, inhibitory activity. FIG. 1B shows the reducing, analytical polyacrylamide gel electrophoresis of 1) material present in the peak of inhibitory activity isolated by gel filtration (silver stain); 2) active material eluted from the preparative gel (silver stain); 3) the same material visualized by autoradiography; 4) autoradiography of the $^{35}$S-labelled species present in the fractions containing inhibitory activity from the heparin-Sepharose column before treatment with N-glycanase (an enzyme that splits the glycopeptide bond between asparagine and glucosamine) and 5) after enzymatic treatment, wherein the 35S label has been removed from the 45,000 molecular weight species.

Figure 2:
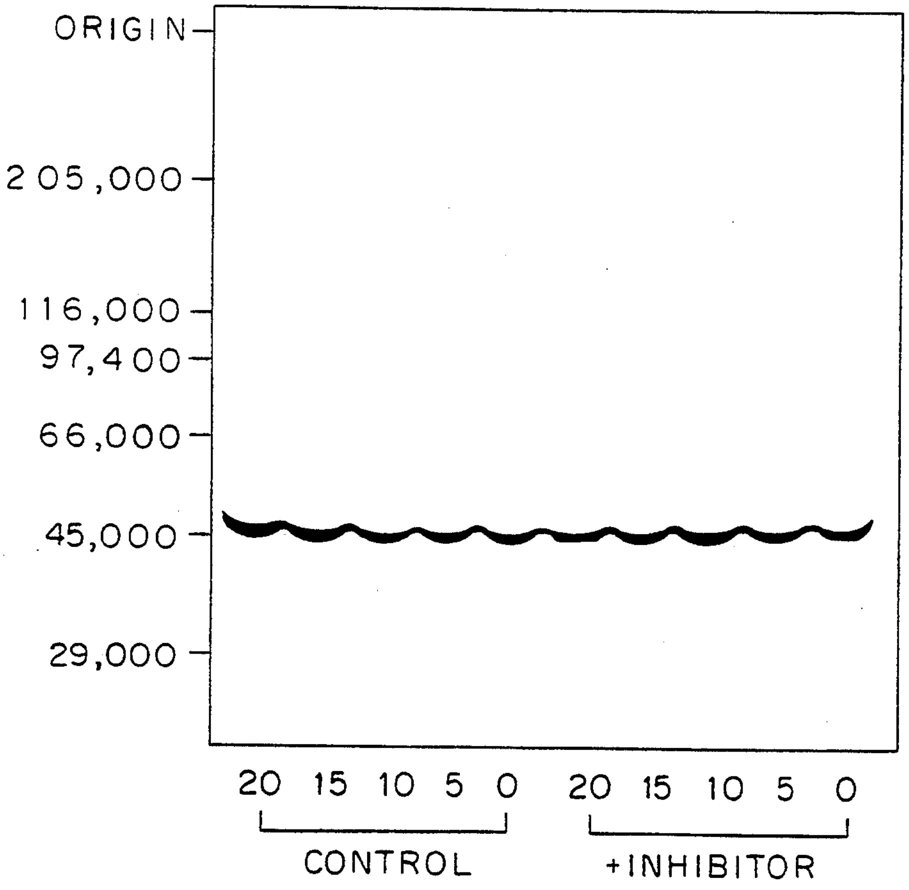
FIG. 2 shows inhibition of factor X activation by the endothelial cell product according to the present invention.

FIG. 2 shows the result of an investigation of the site of action of the inhibitor of the present invention in an enzyme system containing, in addition to factor VII, factor X, the enzyme of coagulation which, when activated by the complex tissue factor-factor VII, converts prothrombin to thrombin, thereby leading to the formation of the fibrin clot. The ability of factor VII to convert factor X to its active form after complexation with tissue factor was estimated by following the degradation of a chromogenic substrate specific for activated factor X, or more directly by following the formation of activated factor X. Factor X activation by the complex tissue factor/factor VII yields a proteolytic fragment and activated factor X. The activation process was followed by immunodetection of the product formed in the presence and in the absence of the endothelial cell inhibitor.

Since in the presence of the inhibitor there is no detectable formation of activated factor X, the block of the pathway must occur at the level of factor VII, or perhaps the inhibition affects tissue factor directly.

Figure 3A:
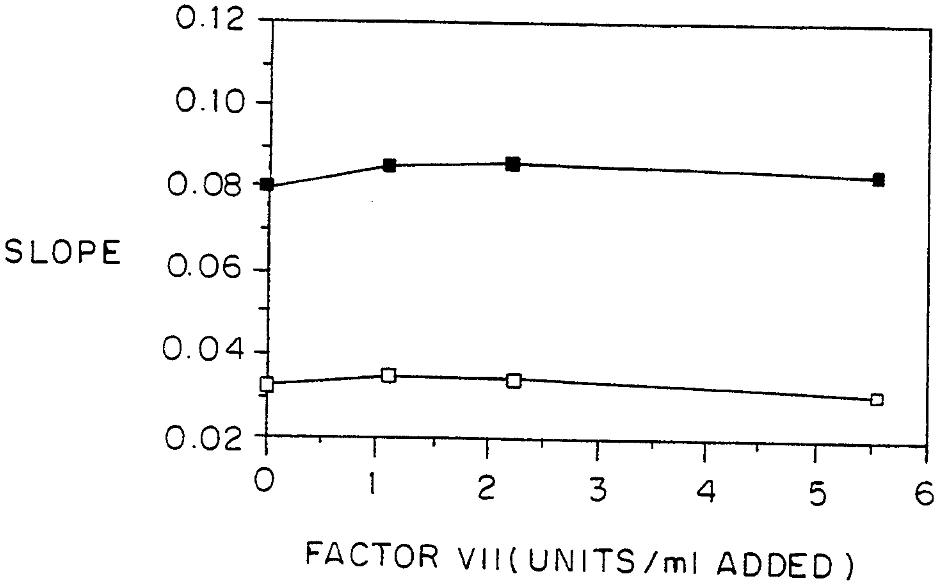
FIGS. 3A and 3B are graphs which show how the addition of increasing amounts of tissue factor overrides the block by the endothelial cell inhibitor.
Figure 3B:
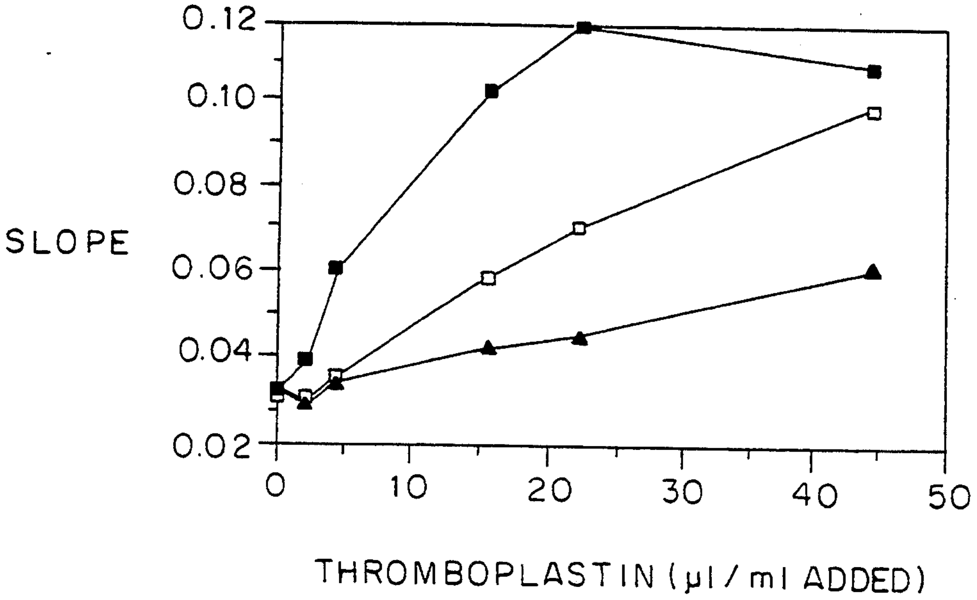

As shown in FIG. 3A, increasing amounts of factor VII do not override the inhibition which is overcome only by higher concentrations of tissue factor. FIG. 3A shows that increasing amounts of factor VII added to an incubation mixture containing the inhibitor fail to relieve the block of the coagulation pathway: ■—■, control samples; □—□, samples containing inhibitor. FIG. 3B shows the same incubation mixture as in FIG. 3A but using increasing amounts of thromboplastin (tissue factor) results in the development of color from the breakdown of the chromogenic substrate by activated factor X: ■—■, control samples; □—□, sample containing 10 $\mu$l of inhibitor; ▲—▲, samples containing 20 $\mu$l of inhibitor.

The site of action of this inhibitor is of special significance, since the complexation of tissue factor with factor VII is seen as a central event in the initiation of the coagulation cascade. Tissue factor-like activity has been detected in endothelial cells when subjected to certain stimuli and also in malignant cells where this procoagulant activity may enhance tumor progression.

Although the glycoproteins of the present invention can be synthesized by endothelial cells, the glycoproteins of the present invention can also be obtained by genetic engineering methods which are well known to those skilled in the art.

The present invention further includes DNA molecules comprising the nucleotide sequence coding for the tissue factor inhibiting protein of the invention, replicable expression vehicles containing said DNA molecules, hosts transformed therewith, and the tissue factor inhibitory protein produced by expression of such transformed hosts. The term "DNA molecules" includes genomic DNA, cDNA, synthetic DNA, and combinations thereof.

The cloning of the tissue factor inhibiting protein of the present invention may be carried out by a variety of techniques. According to one approach, specific antibodies (polyclonal or monoclonal) to the tissue factor inhibiting protein are produced and used to clone the tissue factor inhibiting protein cDNA. This approach includes the following three steps:

a. Preparation of Antibodies

The antibodies to the tissue factor inhibiting protein of the present invention can be produced either by using the substantially purified tissue factor inhibiting protein of the present invention or by using one or more synthetic peptides identical to the known sequence of the protein, e.g., the N-terminal protein sequence, or by fusing one of the possible nucleotide sequences deduced from the amino acid sequence of the tissue factor inhibiting protein to the gene coding for Protein A and expressing the fused Protein A-tissue factor inhibiting protein in *E. coli.*

For obtaining polyclonal antibodies, the substantially purified tissue factor inhibiting protein or the synthetic peptides linked to a carrier protein are injected into a mammal. For the production of monoclonal antibodies, the fused Protein A-tissue factor inhibiting protein synthetic gene is expressed in *E-coli,* the fused protein obtained is purified by affinity chromatography on IgG Sepharose column, and injected into mice. Alternatively, the substantially purified tissue factor inhibiting protein of the present invention is injected into mice.

b. Screening of Tissue Factor Inhibiting Protein Producing Cells

Antibodies to the tissue factor inhibiting protein are used to search for cells producing the tissue factor inhibiting protein by immunofluorescence or by Western blot.

c. Preparation of cDNA from Producing Cells mRNA is extracted from the tissue factor inhibiting protein producing cells and eDNA is prepared using reversed transcriptase. The cDNA is cloned in an expression vector such as λ gT 11 and screened by the use of antibodies. The λ gT 11 expression vector can be used for insertion of DNA up to 7 kb in length at a unique EcoRI site 53 bases upstream from the β-galactosidase termination codon. Therefore, foreign sequence DNA may be inserted into this site and expressed under appropriate conditions as fusion protein. The λ gT 11 expression vector is particularly useful for the construction of cDNA libraries to be screened with antibody probes.

Following another approach, synthetic oligonucleotides or a mixture of synthetic oligonucleotides, whose sequence is derived from the sequence of the protein of the present invention, e.g., the N-terminal amino acid sequence of the tissue factor inhibiting protein, are produced. This oligonucleotide or the mixture of oligonucleotides are used as a probe for cloning the cDNA or the genomic DNA coding for tissue inhibiting protein.

The genomic DNA may optionally include naturally occurring introns. It may be obtained, for example, by extraction from suitable cells and purification by means well known in the art. Suitable DNA preparations, such as human genomic DNA, are enzymatically cleaved by restriction enzymes, or randomly sheared, and the fragments inserted into appropriate recombinant vectors to form a gene library. These vectors can then be screened with synthetic oligonucleotide probes in order to identify a sequence coding for the tissue factor inhibiting protein of the invention.

Alternatively, mRNA is isolated from a cell which expresses the protein of the present invention and is used to produce cDNA by means well known in the art. This cDNA, after conversion to the double-stranded form, may be cloned and the resulting clone screened with an appropriate probe for cDNA coding for the desired sequences. Once the desired clone has been isolated, the cDNA may be manipulated in substantially the same manner as the genomic DNA. However, with cDNA there will be no introns or intervening sequences.

In order to synthesize the oligonucleotides to be used as probes, it is possible either to perform sequence analysis of the intact tissue factor inhibiting protein or to obtain peptide fragments thereof and to characterize their amino acid sequence. In order to obtain peptide fragments, purified protein preparations are subjected to fragmentation, e.g., by digestion with proteases such as trypsin, chymotrypsin, or papain by methods well known in the art (Oike et al., *J. Biol. Chem.* 257: 9751–9758, 1982). The peptide fragments produced by digestion are separated by reverse phase HPLC and sequenced by automatic amino acid sequencing techniques.

As described above, the sequence corresponding to the amino acids at the N-terminal portion of the protein was determined as follows:

$NH_2$-X-X-Glu-Glu-Asp-Glu-Glu-Phe-Thr-X-Ile-Thr-Asp-Ile-Lys-Pro-Pro-Leu-Gln-Lys-Pro-Thr-

Once one or more suitable peptide fragments have been sequenced, or a partial sequence of the protein is determined, the DNA sequences capable of encoding them are examined. Because of the degeneration of the genetic code, more than one codon may be used to encode a particular amino acid, and one or more different oligonucleotides can be produced, each of which would be capable of encoding the tissue factor inhibiting protein peptide fragments [cf. Watson, in *Molecular Biology of the Gene,* 3rd Edition, W. A. Benjamin, Inc., Menlo Park, Calif. (1977), pp. 356–357]. However, only one member of the set contains the nucleotide sequence that is identical to the nucleotide sequence of the gene. Its presence within the set and its capability to hybridize to DNA even in the presence of the other members of the set, makes it possible to use the unfractionated set of oligonucleotides in the same manner in which one would employ a single oligonucleotide to clone the gene that encodes the peptide. The use of such oligonucleotide or set of oligonucleotides containing the theoretical "most probable" sequence capable of encoding the tissue factor inhibiting protein gene fragments, following the "codon usage rules" disclosed by Lathe et al. in *J. Molec. Biol.* 183:1–12, 1985, permits one to identify the sequence of a complementary oligonucleotide or set of oligonucleotides which is capable of hybridizing to the "most probable" sequence encoding the tissue factor inhibiting protein or at least a portion thereof, or a set of such sequences. This oligonucleotide containing such a complementary sequence may then be synthesized and used as a probe to identify and isolate the gene of the tissue factor inhibiting protein of the invention.

Once a suitable oligonucleotide, or set of oligonucleotides, which is capable of encoding a fragment of the tissue factor inhibiting protein gene, or which is complementary to such an oligonucleotide, or set of oligonucleotides, is identified using the abovedescribed procedure, it is synthesized and hybridized to a DNA or, preferably, to a cDNA preparation derived from cells which are capable of expressing the desired gene, preferably after the source of cDNA has been enriched for the desired sequences, e.g., by extracting RNA from cells which produce high levels of the desired gene and then converting it to the corresponding cDNA by using the enzyme reverse transcriptase.

Procedures for hybridization of nucleic acids are common knowledge, and are disclosed, for example, in Maniatis, *Molecular Cloning: A Laboratory Manual,* and Haymes et al., *Nucleic Acid Hybridization: A practical Approach,* IRL Press, Oxford, England (1985). By hybridization with the above nucleotide or set of oligonucleotide probes, it is possible to identify in a cDNA or genomic library the DNA sequences capable of such hybridization, which sequences are then analyzed to determine to what extent they contain encoding sequences for the tissue factor inhibiting protein of the present invention.

By the same or similar techniques, it has been possible to successfully clone the genes for several human proteins, such as the tissue-type plasminogen activator, cf. Pennica et al., *Nature* 301: 214–221, 1983.

The DNA molecules coding for the tissue factor inhibiting factor of the present invention obtained by the above-described methods are then inserted into appropriately constructed expression vectors by techniques well known in the art. Double-stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment with alkaline phosphatases.

In order to be capable of expressing a desired protein, an expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the in promoter of bacteriophage λ the bis promoter of the β-lactamase gene of pBR322, and the CAT promoter of the chloramphenicol acetyl transferase gene of pPR324, etc., or inducible, m such as the prokaryotic promoters including the major right and left promoters of bacteriophage λ Pz and Pm), the trp, recA, lacZ, lacI, ompF, and gal promoters of *E. coli,* or the trp-lac hybrid promoter, etc. (Glick, *J. Ind. Microbiol.* 1: 277-282, 1987).

Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned fomr the initiation codon and complementary to the 3'-terminal sequence of 16S RNA.

For eukaryotic hosts, different transcriptional and translational regulatory sequences may be used, depending upon the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast ga14 gene promoter, etc. Transcriptional initiation regulatory signals may be selected which allow for repression and activation, so that expression of the genes can be modulated.

The DNA molecule comprising the nucleotide sequence coding for the tissue factor inhibiting protein of the invention and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector. The marker may provide for phototrophy to an auxotropic host, biocide resistance, e.g., antibiotics, or heavy metals, such as copper or the like. The selectable marker gene can either be directly linked to the DNA gene sequences to be expressed, or may be introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama in Mol. Cel. Biol. 3: 280, 1983.

In a preferred embodiment, the introduced DNA molecule will be incorporated into a plasmid or vital vector capable of autonomous replication in the recipient host. Factors of importance in selecting a particular plasmid or viral vector include the ease with which the recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli,* such as pBR322, ColE1, pSC101, pACYC 184, etc., (see Maniatis et al., *Molecular Cloning: A Laboratory Manual*); Bacillus plasmids such as pC194, pC221, pT127, etc. (see Gryzcan, *The Molecular Biology of the Bacilli,* Academic Press, NY, 1982, pp 307-329); Streptomyces plasmids including pIJ101 (cf. Kendall et al., *J. Bacteriol.* 169:4177-4183, 1987); Streptomyces bacteriophages such as 0C31 (Chater et al., in *Sixth International Symposium on Actinomycetales. Biology,* Akademiai Kaido, Budapest, Hungary, 1986, pp. 46-54)' and Pseudomonas plasmids (John et al., *Rev. Infect. Dis.* 8: 693-704; and Izaki, *Jpn. J. Bacteriol.* 33: 729-742, 1978).

Preferred eukaryotic plasmids include BPV, vaccinia, SV40, 2-micron circle, etc., or their derivatives. Such plasmids are well known in the art.

Once the vector or DNA sequence containing the constructs has been prepared for expression, the DNA constructs may be introduced into an appropriate host cell by any of a variety of suitable means: transformation, transfection, conjugation, protoplast fusion, electroporation, calcium phosphate-precipitation, direct microinjection, etc.

Host cells to be used in this invention may be either prokaryotic or eukaryotic. Preferred prokaryotic hosts include bacteria such as *E. coli,* Bacillus, Streptomyces, Pseudomonas, Salmonella, Serratia, etc. The most preferred prokaryotic host is *E. coli.* Bacterial hosts of particular interest include *E. coli* K12 strain 294 (ATCC 31446), *E. coli* X1776 (ATCC 31537), *E. coli* W3110 (F-, lambda-, prototropic (ATCC 27325)), and other enterobacteria such as *Salmonella typhimurium* or *Serfaria marcescens* and various Pseudomonas species. Under such conditions, the protein will not be glycosylated. The prokaryotic host must be compatible with the replicon and control sequences in the expression plasmid.

Preferred eukaryotic hosts are mammalian cells, such as human, monkey, mouse, and Chinese hamster ovary (CHO) cells, because they provide post-translational modifications to protein molecules including correct folding or glycosylation at correct sites. Also, yeast cells can carry out post-translational peptide modification including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences, i.e., pre-peptides.

After introduction of the vector, the host cells are grown in a selective medium, which selects for the growth of vector-containing cells. Expression of the cloned gene sequence(s) results in the production of the desired tissue factor inhibiting protein or a fragment thereof. The expressed protein is then isolated and purified in accordance with any purification method including extraction, precipitation, chromatography, electrophoresis, or the like.

A further purification procedure that may be used in preference for purifying the protein of the invention is affinity chromatography. For this purpose, polyclonal or monoclonal antibodies to the tissue factor inhibiting protein are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

The monoclonal antibodies used in the present invention can be prepared using conventional hybridoma techniques, such as disclosed in Kohler et al., Nature 256:495, 1975; Kohler et al., *Eur. J. Immunol* 6:511, 1976. In general, such procedures involve immunizing an animal with the desired purified protein antigen or with a synthetic peptide having the N-terminal sequence of the desired protein conjugated to a suitable carrier, such as bovine serum albumin. Spleen cells of such animals are isolated and fused with a suitable myeloma cell line. After fusion, the resulting hybridoma cells are selectively maintained in HAT medium and then cloned. The hybridoma cells obtained through such a selection are then assayed to identify clones which secrete antibodies capable of binding the tissue factor inhibiting protein. After identification, the desired clone can be grown in bulk, either in suspension culture or in ascitic fluid by injecting the cells into the peritoneum of suitable host mice.

The monoclonal antibodies produced by said hybridomas, after purification and immobilization, are very efficient for the purification of the tissue factor inhibiting protein in affinity purification procedures using an immunoadsorbent column.

Additionally, the monoclonal antibodies prepared with the tissue factor inhibiting protein of the present invention can be labelled by conventional means and used in assays for the proteins of the present invention. These immunological assays are well known to those skilled in the art, and are exemplified by U.S. Pat. No. 4,376,110 to David et al., which patent is hereby incorporated by reference.

Briefly, the immunometric assays that can be performed with either polyclonal or monoclonal antibodies of the present invention can be used to determine the presence and/or concentration of an antigenic substance in a fluid. The assays involve contacting a sample of the fluid with a measured amount of a labelled antibody according to the present invention, and measuring the amount of labelled antibody associated with the antigen. The amount of labelled antibody measured is then related to the amount of labelled antibody measured for a control sample prepared as above, the control sample being known to be free of the antigenic substance, to determine the presence of antigenic substance in the fluid sample, or relating the amount of labelled antibody measured with the amount of labelled antibody measured for samples containing known amounts of antigenie substances prepared as above, to determine the concentration of antigenic substances in the fluid sample. Alternatively, the antigen can be labelled, and the amount brought down can be measured against a standard curve.

The labels for the antibodies can be selected from among the known labels for immunometric assays, e.g., radiolabels, enzyme labels, chemiluminescent labels, fluorescent labels, and the like.

It should be understood that the present invention comprehends tissue factor inhibiting proteins which are effective in inhibiting the initiation of the coagulation process which is promoted by tissue factor.

It should be further understood that the decoyants of the present invention can be modified by extending the polypeptide of the present invention or by adding specific chemical moieties intended to aid in drug design or to permit the tissue factor inhibitors to be used for additional purposes. One such modification would be to extend the polypeptide by moieties intended to affect solubility, e.g., by the addition of a hydrophilic residue, such as serine, or a charged residue, such as glutamic acid. Furthermore, the protein could be extended for the purpose of stabilization and preservation of a desired conformation, such as by adding cysteine residues for the formation of disulfide bridges.

The tissue factor inhibitors may also be modified to make them detectable after administration, such as by radioiodination with a radioactive iodine isotope, directly, or by adding tyrosine for subsequent radioiodination.

Further, alterations of the hemostatic system resulting in an increased incidence of thrombotic disorders is a frequent consequence of neoplasia.

The inhibitors of the present invention are useful in inhibiting intravascular clotting and preventing the formation of fibrin clots both in vitro and in vivo. The inhibitors of the present invention are particularly useful for anticoagulant therapy in prophylaxis of venous thrombosis and as treatment for preventing its extension, as well as to provide a low-dose regiment for prevention of postoperative deep venous thrombosis and pulmonary embolism in patients undergoing major abdominothoracic surgery, particularly those who are at risk of developing thromboembolic disease. The compounds of the present invention can also be used for the propylaxis and treatment of pulmonary embolism and atrial fibrillation with embolization. Additionally, the compounds of the present invention can be used to prevention of clotting in arterial and heart surgery as well as for prevention of cerebral thrombosis in evolving stroke. The compounds of the present invention can be used as an adjunct both in treating coronary occlusion with acute myocardial infarction and in the propylaxis and treatment of peripheral arterial embolism. The compounds can also be employed as an anticoagulant in blood transfusions, extracorporeal circulation, and dialysis procedures and in blood samples for laboratory purposes.

One skilled in the art can determine the amount of the inhibitors of the present invention to be administered, particularly in therapeutic rather than preventative amounts. When the compounds are administered in therapeutic amounts, the dosage should be regulated by frequent blood coagulation tests. If the coagulation test is unduly prolonged, or if there is any indication of hemorrhage, use of the inhibitor would be discontinued.

The inhibitors of the present invention can be administered in compositions containing the active ingredient in a pharmaceutically acceptable carrier. Determination of the effective amounts is within the skill of the art.

In addition to the inhibitors of the present invention, these pharmaceutical compositions may contain suitable pharmaceutically acceptable carriers comprising excipients and auxiliaries which facilitate processing of the active compounds into preparations which can be used pharmaceutically. Preferably, the preparations contain from about 0.1 to about 99 percent of active compound, together with the excipient.

The pharmaceutical preparations of the present invention can be manufactured in a manner which is itself known, for example, by means of conventional mixing, dissolving, or lypophilizing processes. Suitable formulations for parenteral administration include aqueous solutions of the active compounds in water-soluble form. In addition, suspensions of the active compounds as appropriate oily injection suspensions may be administered. Suitable lipohilic solvent or vehicles include fatty oils such as sesame oil, or synthetic fatty acid esters such as ethyl oleate or triglycerides. Aqueous injection suspensions may contain substances which increase the viscosity of the suspension such as sodium carboxymethyl cellulose, sorbitol, and/or dextran. Optionally, the suspension may also contain stabilizers. The tissue factor inhibitors of the present invention may also be administered in the form of liposomes, pharmaceutical compositions in which the active ingredient is contained either dispersed or variously present in corpuscles consisting of aqueous concentric layers adherent to lipidic layers. The active ingredient may be present both in the aqueous layer and in the lipidic layer, or, in any event, in the non-homogeneous system generally known as a liposomic suspension.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, as water-soluble salts. In addition, suspension of the active compounds as appropriate oily injection suspensions may be administered. Suitable lipophilic solvents or vehicles include fatty oils, for example, sesame oil, or synthetic fatty acid esters, such as ethyl oleate or triglycerides.

Aqueous injection suspensions may contain substances which increase the viscosity of the suspension such as sodium carboxymethyl cellulose, sorbitol, and/or dextran. Optionally, the suspension may also contain stabilizers.

The compounds of the present invention may be immobilized to affinity matrices and biological molecules by well established procedures. For example, these compounds may be immobilized to an affinity matrix by treatment of such a mixture with dicyclohexylcarboi-imide in a suitable solvent, or by glutaraldehyde crosslinking.

The compounds of the present invention can also be administered in the form of liposomes, pharmaceutical compositions in which the active ingredient is contained either dispersed or variously present in corpuscles consisting of aqueous concentric layers adherent to lipidic layers (hydrophobic). The drug may be present both in the aqueous layer and in the lipidic one (inside or outside) or, in any event, in the non-homogeneous system generally known as a liposomic suspension.

The inhibitor of the present invention can be administered to a patient at risk for clot formation in effective amounts to prevent initiation of the clotting mechanism. Alternatively, the inhibitors of the present invention can be used therapeutically to treat coronary occlusion with acute myocardial infarction and peripheral arterial embolism. Generally, amounts ranging from about 1 mg to about 12 mg a day can be administered to prevent clotting, and preferably from about 4 to about 6 mg per day. Effective amounts to be administered are dependent upon the individual patient, and can readily be determined by one skilled in the art.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A purified antibody having an antibody binding region specific to an epitope of a purified and isolated tissue factor inhibiting protein, said protein comprising a sulfated glycoprotein having a molecular weight of about 45 kDa, wherein (a) said protein has the ability to inhibit the activity of tissue factor; and (b) said glycoprotein includes the amino acid sequence:

$X_1$-$X_2$-Glu-Glu-Asp-Glu-Glu-Phe-Thr-$X_3$-Ile-Thr-Asp-Ile-Lys-Pro-Pro-Leu-Gln-Lys-Pro-Thr, where $X_1$, $X_2$, and $X_3$ can be the same or different and denote any amino acid.

2. An antibody according to claim 1, wherein said tissue factor inhibiting protein is in the form of a salt.

3. An antibody according to claim 1, wherein said tissue factor inhibiting protein is a recombinant protein.

4. A method for assaying for tissue factor inactivating protein comprising contacting a sample fluid with a labelled antibody according to claim 22 to form a conjugate of the tissue factor inhibiting protein and the antibody, and assaying the conjugate to determine the presence and amount of the tissue factor inhibiting protein.

5. The method according to claim 4 wherein the label is a radioactive label.

6. The method according to claim 4 wherein the label is an enzyme label.

7. The method according to claim 4 wherein the label is a chemiluminescent label.

8. The method according to claim 4 wherein the label is a fluorescent label.

9. The method of claim 4 wherein the antibody is a monoclonal antibody.

* * * * *